United States Patent
Tsuang et al.

(10) Patent No.: US 8,470,299 B2
(45) Date of Patent: Jun. 25, 2013

(54) BIOMARKERS FOR PSYCHOSIS

(75) Inventors: Ming T. Tsuang, La Jolla, CA (US); Ian P. Everall, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 318 days.

(21) Appl. No.: 12/600,119

(22) PCT Filed: May 15, 2008

(86) PCT No.: PCT/US2008/006212
§ 371 (c)(1),
(2), (4) Date: Aug. 13, 2010

(87) PCT Pub. No.: WO2008/143919
PCT Pub. Date: Nov. 27, 2008

(65) Prior Publication Data
US 2010/0297625 A1 Nov. 25, 2010

Related U.S. Application Data

(60) Provisional application No. 60/938,128, filed on May 15, 2007.

(51) Int. Cl.
*C12Q 1/68* (2006.01)
*G01N 33/50* (2006.01)
*G01N 33/68* (2006.01)

(52) U.S. Cl.
USPC .............................. 424/9.1; 435/6.1; 435/7.95

(58) Field of Classification Search
None
See application file for complete search history.

(56) References Cited

FOREIGN PATENT DOCUMENTS

WO  WO2006/089062 A2 * 8/2006
WO  WO-2006089062 A2   8/2006

OTHER PUBLICATIONS

Glatt et al., PNAS, 102(43): 15533-15538, Oct. 25, 2005.*
Tian et al., Neuroscience Letters, 411:123-127, epublished Nov. 13, 2006.*
Machado et al., Neuroscience Letters, 410: 198-202, 2006.*
Vukosavic et al., Neuroscience Research, 40:133-140, 2001.*
Perrone-Bizzozero et al., PNAS, 93:14182-14187, Nov. 1996.*
"International Application Serial No. PCT/US2008/006212, International Search Report and Written Opinion Mailed on Oct. 16, 2008", 17pgs.
Glatt, S. J, et al., "Comparitive Gene Expression Analysis of Blood and Brain Provides Concurrent Validation of SELENBP1 Up-Regulation in Schizophrenia", *Proceedings of The National Academy of Sciences of The United States of America*, vol. 102,No. 3, (Oct. 25, 2005), pp. 15533-15538.
Kanazawa, T., et al., "The Utility of SELENBP1 Gene Expression as a Biomarker for Major Psychotic Disorders: Replication in Schizophrenia and Extension to Bipolar Disorder witih Psychosis", *American Journal of Medical Genetics Part B (Neuropsychiatric Genetics*, AJMB-07-0187.R1(30664), (2007), 4 pages.
Tian, S. Y, et al., "Immunoreactivity of 43 KDa Growth-associated protein is decreased in Post Mortem hippocampus of bipolar disorder and Schizophrenia", *Neuroscience Letters*, (Jan. 10, 2007), 123-127.
Grant, N.J., et al., "Noradrenergic but not Adrenergic Chromaffin Cells in the Adrenal Gland Express Neuromodulin (GAP-43)", Eur. J. Neurosci., (1992), (Abstract).
Kruger, L., et al., "GAP-43 mRNA Localization in the Rat Hippocampus CA3 Field", Brain Res Mol Brain Res., (Apr. 13, 1992), (Abstract).
Stocker, K.M., et al., "GAP-43 in Non-Neuronal Cells of the Embryonic Chick Limb: Clues to Function", Perspect Dev Neurobiol., (1992), (Abstract).
Verhaagen, J., et al., "The Expression of the Growth Associated Protein B50/GAP43 in the Olfactory System of Neonatal and Adult Rats", J. Neurosci., (Feb. 9, 1989), (Abstract).
Yamamoto, M., et al., "Gene Expression of a Neuronal Growth-Associated Protein, GAP-43, in the Paraganglionic Cartoid Body as well as in the Autonomic Ganglia of Normal Adult Rats", Neurosci Lett., (Sep. 18, 1990), (Abstract).

* cited by examiner

*Primary Examiner* — Daniel E Kolker
*Assistant Examiner* — Stacey N Macfarlane
(74) *Attorney, Agent, or Firm* — Schwegman Lundberg & Woessner, P.A.

(57) ABSTRACT

The present invention relates generally to the diagnosis of psychosis, schizophrenia and bipolar disorder, including psychotic bipolar disorder.

15 Claims, 1 Drawing Sheet

BIOMARKERS FOR PSYCHOSIS

REFERENCE TO RELATED APPLICATIONS

This application is a U.S. National Stage Filing under 35 U.S.C. 371 from International Patent Application Serial No. PCT/US2008/006212, filed May 15, 2008, and published on Nov. 27, 2008, as WO 2008/143919 A1, which claims priority to U.S. Provisional Patent Application Ser. No. 60/938,128, which was filed on May 15, 2007 and the contents of which are incorporated herein in their entirety by reference.

BACKGROUND OF THE INVENTION

Identification of biomarkers for psychiatric disorders would provide a significant advance in the diagnostic procedure, which is currently dependent on the presentation of clinical symptoms over an extended period of time. Since disorders such as schizophrenia and bipolar disorder are also highly heritable disorders, current pursuits of biomarkers for these disorders have focused on gene-based biomarkers, such as mRNA expression levels. Previous gene expression biomarker studies have identified candidate genes now implicated (though none universally) in the etiology of schizophrenia and bipolar disorder. While some of these candidates are in keeping with previous cellular and molecular studies of psychiatric disorders (Mimics et al. 2001; Vawter et al. 2002; Chen and Chen 2005), novel candidates are also being identified. For example, using microarray analysis, the expression of selenium binding protein 1 gene (SELENBP1) was increased in the blood and brain of patients with schizophrenia (Glatt et al. 2005; finding confirmed in blood using quantitative real-time PCT (QPCR)).

SUMMARY OF THE INVENTION

The present invention provides methods to diagnose psychosis, schizophrenia and bipolar disorder, including psychotic bipolar disorder. For example, one embodiment provides a method to diagnose psychosis comprising determining an amount of SELENBP1 in a first biological sample from a subject, wherein a higher amount of SELENBP1 in the first biological sample than an amount of SELENBP1 in a second biological sample from a non-psychotic individual indicates psychosis in said subject. In one embodiment, the subject has schizophrenia. In another embodiment, the subject has bipolar disorder.

One embodiment provides a method to diagnose bipolar disorder comprising determining an amount of growth associated protein 43 (GAP-43) in a first biological sample from a subject, wherein a higher amount of GAP-43 in the first biological sample than an amount of GAP-43 in a second biological sample from an individual without bipolar disorder indicates bipolar disorder in said subject. In one embodiment, the bipolar disorder is non-psychotic bipolar disorder. In another embodiment, the bipolar disorder is psychotic bipolar disorder.

One embodiment, provides a method to diagnose psychotic bipolar disorder comprising determining an amount of SELENBP1 and growth associated protein 43 (GAP-43) in a first biological sample from a subject, wherein a higher amount of SELENBP1 and GAP-43 in the first biological sample than an amount of SELENBP1 and GAP-43 in a second biological sample from an individual without psychotic bipolar disorder indicates psychotic bipolar disorder in said subject.

In one embodiment, the subject and individual are mammalian, such as human. In another embodiment, the first and second samples comprise brain.

In one embodiment, the amount of SELENBP1 is determined by measuring the amount of SELENBP1 mRNA. In another embodiment, the amount of SELENBP1 is determined by measuring the amount of SELENBP1 protein.

In one embodiment, the amount of GAP-43 is determined by measuring the amount of GAP-43 mRNA. In another embodiment, the amount of GAP-43 is determined by measuring the amount of GAP-43 protein.

In one embodiment, the method confirms a previous diagnosis (e.g., a clinical or psychological diagnosis) of psychosis, bipolar disorder or psychotic bipolar disorder.

BRIEF DESCRIPTION OF THE DRAWINGS

In FIG. 1A the mean (±two SEM) for the gene expression of SELENBP1 (relative to GADPH) as estimated by the delta C(T) method is shown for Schizophrenia and Normal Controls. Lower mean C(T) indicates higher gene expression.

DETAILED DESCRIPTION OF THE INVENTION

Figure 1A:
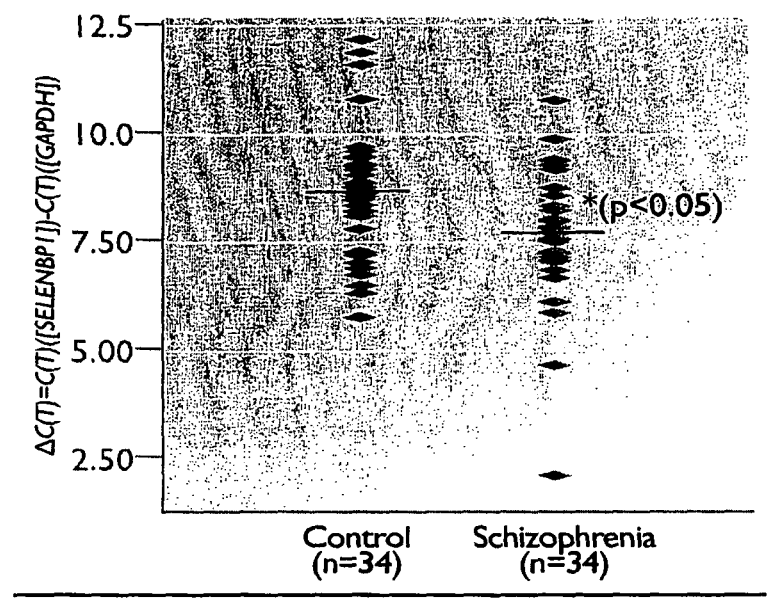
FIGS. 1A and B depict delta C(T) for SELENBP1 Gene Expression by Presence of Psychosis and by Clinical Disease Group (Schizophrenia and Normal Controls).

Using microarray analysis, the expression of selenium binding protein 1 gene (SELENBP1) was demonstrated to be increased in the blood and brain of patients with schizophrenia (Glatt et al. 2005), a finding that was confirmed in the blood using quantitative real-time PCR (QPCR). Selenium binding proteins have been shown to co-localize with g-actin at the growing tips of SY5Y neuroblastoma cells (Miyaguchi 2004), which indicates the potential for SELENBP1 to be associated with the growth and remodeling of neurites. These results are of interest in light of alterations in dendritic and synaptic proteins noted in both bipolar disorder and schizophrenia (Harrison 1999; 2002). Moreover the gene locates in 1q21-q22, which has been regarded as a strong susceptibility loci by several papers (Brzustowicz et al. 2000; Jurewicz et al. 2001). As such, gene expression biomarker studies of schizophrenia or bipolar disorder can shed light on the etiology of these disease; however, an underappreciated aspect of such studies is that they can also identify biological commonalities between disorders currently considered to be separate entities. To date, however, gene expression biomarker studies of common clinical characteristics between schizophrenia and bipolar disorder (e.g., physchosis) have not been widely implemented.

The investigation of psychotic illness that occurs in both schizophrenia and bipolar illness is described herein by quantifying SELENBP1 gene expression in the brain using QPCR. Of note, over one half of the bipolar disorder cases had documented episodes of psychosis (including delusions, hallucinations, catatonia, disorganized speech or behavior), which enabled the examination of gene expression changes by the presence or absence of psychosis as well as by clinical diagnosis. mRNA samples prepared from the dorsolateral prefrontal cortex (dlPFC, BA 46) of patients with schizophrenia and bipolar disorder as well as matched controls were utilized.

A significant increase in SELENBP1 gene expression in individuals with an episode of psychosis was found; SELENBP1 gene expression was also elevated in schizophrenia, as well as in psychotic bipolar cases, which points to a common mechanism of development of psychosis regardless of clinical group.

GAP-43 was additionally examined and shown to increase expression in bipolar disorder (psychotic and non-psychotic). Assessment of expression of these two genes, SELENNBP1 and GAP-43, can be a biomarker for psychosis and bipolar disease.

DEFINITIONS

A "subject" and/or "individual" is a vertebrate, preferably a mammal, more preferably a human. Mammals include, but are not limited to, humans, farm animals, sport animals and pets.

As used herein, "biological sample" refers to any physiological fluid or tissue including, but not limited to, a sample from brain, cerebrospinal fluid, blood, plasma, serum, urine, saliva and the like.

Exemplary means for detecting and/or quantitating SELENBP1 or GAP-43 amounts in a sample include PCR, including QPCR, microarray analysis, Norther blot analysis, dot blot analysis, affinity chromatography, Western blot analysis, immunoprecipitation analysis, and immunoassays, including ELISAs (enzyme-linked immunosorbent assays), RIA (radioimmunoassay), competitive EIA or dual antibody sandwich assays. The antibodies, oligonucleotides or other binding molecules employed in the assays may be labeled or unlabeled for ease of detection (e.g., radionucleotides, enzymes, fluorescers, chemiluminescers, enzyme substrates or co-factors, enzyme inhibitors, particles, dyes and the like).

The terms "comprises", "comprising", and the like can have the meaning ascribed to them in U.S. Patent Law and can mean "includes", "including" and the like. As used herein, "including" or "includes" or the like means including, without limitation.

Schizophrenia

Schizophrenia is a psychiatric diagnosis that describes a mental illness characterized by impairments in the perception or expression of reality, most commonly manifesting as auditory hallucinations, paranoid or bizarre delusions or disorganized speech and thinking in the context of significant social or occupational dysfunction. Onset of symptoms typically occurs in young adulthood, with approximately 0.4-0.6% of the population affected. Diagnosis is based on the patient's self-reported experiences and observed behavior.

Studies suggest that genetics, early environment, neurobiology and psychological and social processes are important contributory factors. Current psychiatric research is focused on the role of neurobiology, but no single organic cause has been found yet. Despite its etymology, schizophrenia is not synonymous with dissociative identity disorder, previously known as multiple personality disorder or split personality; in popular culture the two are often confused.

Increased dopaminergic activity in the mesolimbic pathway of the brain is a consistent finding. The mainstay of treatment is pharmacotherapy with antipsychotic medications; these primarily work by suppressing dopamine activity. Psychotherapy, vocational and social rehabilitation are also important. In more serious cases—where there is risk to self and others—involuntary hospitalization may be necessary.

The disorder is primarily thought to affect cognition, but it also usually contributes to chronic problems with behavior and emotion. People diagnosed with schizophrenia are likely to be diagnosed with comorbid conditions, including clinical depression and anxiety disorders. Social problems, such as long-term unemployment, poverty and homelessness, are common and life expectancy is decreased by 10 to 12 years than those without schizophrenia.

Diagnosis is based on the self-reported experiences of the person as well as abnormalities in behavior reported by family members, friends or co-workers, followed by secondary signs observed by a psychiatrist, social worker, clinical psychologist or other clinician in a clinical assessment. There is a list of criteria that is usually met for someone to be so diagnosed. These depend on both the presence and duration of certain signs and symptoms.

An initial assessment includes a comprehensive history and physical examination by a physician. Tests are carried out to exclude medical illnesses which may rarely present with psychotic schizophrenia-like symptoms. These include blood tests measuring TSH to exclude hypo- or hyperthyroidism, basic electrolytes and serum calcium to rule out a metabolic disturbance, full blood count including ESR to rule out a systemic infection or chronic disease, and serology to exclude syphilis or HIV infection. Two commonly ordered investigations are EEG to exclude epilepsy, and a CT scan of the head to exclude brain lesions. It is important to rule out a delirium which can be distinguished by visual hallucinations, acute onset and fluctuating level of consciousness and indicates an underlying medical illness. There are several psychiatric illnesses which may present with psychotic symptoms other than schizophrenia. These include bipolar disorder, borderline personality disorder, drug intoxication, brief drug-induced psychosis, and schizophreniform disorder.

Criteria for diagnosing schizophrenia are can be found in the American Psychiatric Association's Diagnostic and Statistical Manual of Mental Disorders, the current version being DSM-IV-TR, and the World Health Organization's International Statistical Classification of Diseases and Related Health Problems, currently the ICD-10. The WHO has developed the tool SCAN (Schedules for Clinical Assessment in Neuropsychiatry) which can be used for diagnosing a number of psychiatric conditions, including schizophrenia.

To be diagnosed with schizophrenia, a person usually displays two or more of the following, each present for a significant portion of time during a one-month period (or less, if successfully treated)—delusions; hallucinations; disorganized speech (e.g., frequent derailment or incoherence; speaking in abstracts); grossly disorganized behavior (e.g. dressing inappropriately, crying frequently) or catatonic behavior; negative symptoms, i.e., affective flattening (lack or decline in emotional response), alogia (lack or decline in speech), or avolition (lack or decline in motivation). Note, generally only one of these symptoms is required if delusions are bizarre or hallucinations consist of hearing one voice participating in a running commentary of the patient's actions or of hearing two or more voices conversing with each other. Additionally there may be social/occupational dysfunction—for a significant portion of the time since the onset of the disturbance, one or more major areas of functioning such as work, interpersonal relations, or self-care, are markedly below the level achieved prior to the onset.

Bipolar Disorder

Bipolar disorder is not a single disorder, but a category of mood disorders defined by the presence of one or more episodes of abnormally elevated mood, clinically referred to as mania. Individuals who experience manic episodes also commonly experience depressive episodes or symptoms, or mixed episodes in which features of both mania and depression are present. These episodes are normally separated by periods of normal mood, but in some patients, depression and mania may rapidly alternate, known as rapid cycling. Manic episodes can sometimes lead to psychotic symptoms such as delusions and hallucinations. The disorder has been subdivided into bipolar I, bipolar II, bipolar NOS, and cyclothymia based on the type and severity of mood episodes experienced.

Also called bipolar affective disorder until recently, the current name is of fairly recent origin and refers to the cycling between high and low episodes; it has replaced the older term manic-depressive illness.

Onset of symptoms generally occurs in young adulthood. Diagnosis is based on the person's self-reported experiences, as well as observed behavior. Episodes of illness are associated with distress and disruption, and a relatively high risk of suicide. Studies suggest that genetics, early environment, neurobiology, and psychological and social processes are important contributory factors. Psychiatric research is focused on the role of neurobiology, but a clear organic cause has not been found. Bipolar disorder is usually treated with medications and/or therapy or counseling. The mainstay of medication are a number of drugs termed 'mood stabilizers', in particular lithium and sodium valproate; these are a group of unrelated medications used to prevent relapses of further episodes. Antipsychotic medications, sometimes called neuroleptics, in particular olanzapine, are used in the treatment of manic episodes and in maintenance. The benefits of using antidepressants in depressive episodes is unclear. In serious cases where there is risk to self and others involuntary hospitalization may be necessary; these generally involve severe manic episodes with dangerous behavior or depressive episodes with suicidal ideation.

Diagnosis is based on the self-reported experiences of the patient as well as abnormalities in behavior reported by family members, friends or co-workers, followed by secondary signs observed by a psychiatrist, nurse, social worker, clinical psychologist or other clinician in a clinical assessment. There is a list of criteria that must be met for someone to be so diagnosed. These depend on both the presence, and duration of certain signs and symptoms.

An initial assessment includes a comprehensive history and physical examination by a physician. Tests are carried out to exclude medical illnesses which may rarely present with psychiatric symptoms. These include blood tests measuring TSH to exclude hypo- or hyperthyroidism, basic electrolytes and serum calcium to rule out a metabolic disturbance, full blood count including ESR to rule out a systemic infection or chronic disease, and serology to exclude syphilis or HIV infection; two commonly ordered investigations are EEG to exclude epilepsy, and a CT scan of the head to exclude brain lesions. There are several psychiatric illnesses which may present with similar symptoms; these include schizophrenia, drug intoxication, brief drug-induced psychosis, schizophreniform disorder and borderline personality disorder. Alternately, patients currently in a hypomanic or mixed affective episode may display symptoms resembling borderline personality disorder.

The last is relevant as both diagnoses involve symptoms commonly known as "mood swings". In bipolar disorder, the term refers to the cyclic episodes of elevated and depressed mood which generally last weeks or months (notwithstanding Rapid Cycling variant of greater than four episodes a year). The term in borderline personality refers to the marked lability and reactivity of mood, known as emotional dysregulation, due to response to external psychosocial and intrapsychic stressors; these may arise or subside suddenly and dramatically and last for seconds, minutes, hours or days. A bipolar depression is generally more pervasive with sleep, appetite disturbance and nonreactive mood, whereas the mood in dysthymia of borderline personality remains markedly reactive and sleep disturbance not acute.

Criteria for diagnosing bipolar disorder are found in American Psychiatric Association's Diagnostic and Statistical Manual of Mental Disorders, the current version being DSM-IV-TR, and the World Health Organization's International Statistical Classification of Diseases and Related Health Problems, currently the ICD-10.

Currently there is no consensus as to how many types of bipolar disorder exist. In DSM-IV-TR and ICD-10, bipolar disorder is conceptualized as a spectrum of disorders occurring on a continuum. The DSM-IV-TR lists four types of mood disorders which fit into the bipolar categories: Bipolar I, Bipolar II, Cyclothymia, and Bipolar Disorder NOS (Not Otherwise Specified).

In Bipolar I disorder, an individual has experienced one or more manic episodes with or without major depressive episodes. For a diagnosis of Bipolar I disorder according to the DSM-IV-TR, there requires one or more manic or mixed episodes. A depressive episode is not required for the diagnosis of Bipolar I disorder, but it frequently occurs.

Bipolar II disorder is characterized by hypomanic episodes as well as at least one major depressive episode. Hypomanic episodes do not go to the extremes of mania (i.e., do not cause social or occupational impairment, and without psychosis), and this can make Bipolar II more difficult to diagnose, since the hypomanic episodes may simply appear as a period of successful high productivity and is reported less frequently than a distressing depression. For both disorders, there are a number of specifiers that indicate the presentation and course of the disorder, including "chronic," "rapid cycling," "catatonic" and "melancholic."

Cyclothymia involves a presence or history of hypomanic episodes with periods of depression that do not meet criteria for major depressive episodes. A diagnosis of Cyclothymic Disorder requires the presence of numerous hypomanic episodes, intermingled with depressive episodes that do not meet full criteria for major depressive episodes. The main idea here is that there is a low-grade cycling of mood which appears to the observer as a personality trait, but interferes with functioning.

Bipolar Disorder Not Otherwise Specified is a catch-all diagnosis that is used to indicate bipolar illness that does not fit into the other diagnostic categories. If an individual clearly seems to be suffering from some type of bipolar disorder but does not meet the criteria for one of the subtypes above, he or she receives a diagnosis of Bipolar Disorder NOS (Not Otherwise Specified).

Psychosis

Psychosis is a generic psychiatric term for a mental state often described as involving a "loss of contact with reality." People suffering from it are said to be psychotic.

People experiencing psychosis may report hallucinations or delusional beliefs, and may exhibit personality changes and disorganized thinking. This may be accompanied by unusual or bizarre behavior, as well as difficulty with social interaction and impairment in carrying out the activities of daily living.

In medical practice today, a descriptive approach to psychosis is used, based on behavioral and clinical observations. This approach is adopted in the standard guide to psychiatric diagnoses, the Diagnostic and Statistical Manual of Mental Disorders (DSM). According to the DSM-IV-TR, the term psychosis has had many definitions in the past, both broad and narrow. The broadest was not being able to meet the demands of everyday life. The narrowest was delusions or hallucinations without insight. A middle ground may be delusions, hallucinations with or with out insight, and well as disorganized behavior or speech. Thus, psychosis can be a symptom of mental illness. For example, people with schizophrenia often experience psychosis, but so can people with bipolar disorder (manic depression), unipolar depression, delirium, or drug withdrawal. People diagnosed with these conditions can also have long periods without psychosis, and some may never experience them again. Conversely, psychosis can occur in people who do not have chronic mental illness (e.g., due to an adverse drug reaction or extreme stress)

The DSM-IV-TR lists 9 formal psychotic disorders, but many other disorders may have psychotic symptoms. The formal psychotic disorders are: Schizophrenia; Schizoaffective disorder; Schizophreniform disorder; Brief psychotic disorder; Delusional; Shared psychotic disorder (Folie à deux); Substance induced psychosis; Psychosis due to a general medical condition; and Psychosis—Not otherwise specified.

Functional causes of psychosis are believed to include the following: schizophrenia; bipolar disorder; severe clinical depression; severe psychosocial stress; sleep deprivation.

A psychotic episode can be significantly affected by mood. For example, people experiencing a psychotic episode in the context of depression may experience persecutory or self-blaming delusions or hallucinations, while people experiencing a psychotic episode in the context of mania may form grandiose delusions.

EXAMPLE

The following example is provided in order to demonstrate and further illustrate certain embodiments and aspects of the present invention and is not to be construed as limiting the scope thereof.

Example 1

Materials and Methods

In this study, psychotic illness that occurs in both schizophrenia and bipolar illness was investigated by quantifying SELENBP1 gene expression in the brain using QPCR (primers). Over one-half of the bipolar disorder cases in this study had documented episodes of psychosis (including delusions, hallucinations, catatonia, disorganized speech or behavior) (Potash et al. 2003; Ketter et al. 2004), which enabled the examination of gene expression changes in the presence or absence of psychosis as well as across clinical diagnoses. mRNA samples prepared from the dorsolateral prefrontal cortex (dlPFC, BA 46) of patients with schizophrenia and bipolar disorder was used as well as matched controls.

RNA samples from fresh-frozen dlPFC were obtained from samples in the Stanley Array Collection maintained by the Stanley Medical Research Foundation. The Array Collection consists of brains from 35 patients with schizophrenia (SCZ), 35 with bipolar disorder (BP) and 35 matched non-psychiatric controls (NC), which are described elsewhere (Xu et al. 2005). One bipolar disorder case (Stanely ID #259) was excluded from the study due to cerebral autosomal dominant arteriopathy with subcortical infarcts and leukoencephalopathy, which may have confounded the gene expression findings. In addition RNA from one sample from each of the groups (Stanely ID #289, 369, 438) failed to yield sufficient QPCR signal and these samples were therefore also excluded from the analyses. The demographic variables of all included samples are summarized below in Table 1. Of the bipolar cases, 20 were diagnosed as psychotic, which together with the 34 schizophrenia cases provided 54 cases with psychosis and 45 who had not been psychotic. The Stanley Foundation assessed RNA concentrations (1.964±1.216 µg/µl) using an Agilent 2100 Bioanalyzer (Agilent, USA). Concentrations of RNA were confirmed by a UV spectrophotometer at 260 nM/280 nM in order to accurately load 1 µg of RNA for cDNA synthesis. In Table 1 (below), the concentrations of mRNA are also included. cDNA synthesis was then carried out using the iScript cDNA synthesis kit (Bio-Rad, USA) according to the standard protocol.

TABLE 1

Demographic Data for Patient, Sample, and Clinical Variables

|  | SCZ (n = 34) | BPD (n = 33) | NC (n = 34) |
|---|---|---|---|
| Patient Variables |  |  |  |
| Age at death (mean year ± SD) | 42.8 ± 8.51 | 45.4 ± 10.83 | 44.5 ± 7.52 |
| Sex (M/F) | 26/8 | 15/18 | 25/9 |
| Ancestry (Caucasian/Other) | 33/1 | 32/1 | 34/0 |
| Sample Variables |  |  |  |
| Refrigerator interval (mean hour ± SD) | 6.03 ± 4.28 | 9.97 ± 10.6 | 3.61 ± 2.68 |
| Death by suicide (n) | 6 | 15 | 0 |
| PMI (mean hour ± SD) | 31.5 ± 15.75 | 38 ± 18.90 | 28.71 ± 12.43 |
| pH (mean ± SD) | 6.47 ± 0.246 | 6.44 ± 0.301 | 6.61 ± 0.269 |
| Left brain (n) | 16 | 18 | 16 |
| Right brain (n) | 18 | 15 | 18 |
| Brain weight (mean g ± SD) | 1,441 ± 109 | 1,398 ± 142 | 1,436 ± 143 |
| RNA concentration (mean µg/ul ± SD) | 0.942 ± 0.695 | 0.760 ± 0.764 | 0.699 ± 0.564 |
| Clinical Variables |  |  |  |
| Age of onset (mean year ± SD) | 20.9 ± 5.80 | 25.5 ± 9.21 |  |
| Duration of illness (mean year ± SD) | 21.8 ± 9.78 | 19.9 ± 9.64 |  |
| Time in hospital (mean year ± SD) | 1.26 ± 2.28 | 0.53 ± 1.41 |  |
| Alcohol abuse At TOD (n) | 12 | 10 | 2 |
| Drug abuse At TOD (n) | 9 | 8 | 1 |
| Smoking at TOD (n: Yes/No/Unknown) | 23/4/7 | 15/6/12 | 9/9/16 |
| Psychotic feature (n: Yes/No/Unknown) | 34/0/0 | 20/11/2 | 0/34/0 |
| Lifetime antipsychotics (FE ± SD) | 87,487 ± 10,747 | 9,913 ± 23,529 |  |

Abbreviations: SCZ, schizophrenia; BPD, bipolar disorder; NC, non-psychiatric control; PMI, postmortem interval; TOD, time of death; FE, fluphenazine equivalents (mg).

QPCR was performed under standard conditions using the iQ5 real-time system (Bio-Rad, USA) together with Taqman Gene Expression Assay kits (Applied Biosystems, USA) specific for SELENBP1 (Canales et al. 2006). Assays containing FAM dye-labeled probes and random octomers for synthesis of SELENBP1 were utilized (Assay ID: Hs00187625_m1), and two housekeeping genes, ACTB (part #:4352668) and GAPDH (part#:4352666), which previously have been found to be stable in post-mortem brain RNA samples (Mimmack et al. 2002; Dempster et al. 2006). Dilution series (0.1 ng, 1 ng, 10 ng, and 100 ng) for ACTB and GAPDH were carried out in five randomly chosen cases to determine the appropriate amount of cDNA for QPCR runs. Loading 10 ng of cDNA produced consistent results across cases and this concentration was used for assessing gene expression across groups. Within each plate RNase-free water was loaded as a negative control, and cases were run as duplicates within individual 96-well plates to control for variability in pipetting and cycling conditions. The average of the duplicates per subject was utilized as the value of C(T) for that individual. GAPDH was employed as the housekeeping gene for normalizing individual gene expression values prior to statistical analyses. To calculate relative fold-changes between patient and control samples, the delta C(T) method was used, calculated as follows: $\{[C(T)(SELENBP1)]-[C(T)(GAPDH)]\}$ (Livak and Schmittgen, 2001).

Results

In the first step of analysis, demographic variables (Patient, Sample, and Clinical Variables; the detail is shown in Table 1) were identified that predicted gene expression at the P<0.10 level using Pearson's correlations. These variables, together with variables that could potentially affect gene expression (Harrison et al 1995; Kingsbury et al. 1995; Preece and Cairns 2003; Lipska et al. 2006; Mufson et al. 2006), were then controlled for in the final statistical model. For comparisons of SELENBP1 in either the presence of psychosis or clinical disease groups, a univariate analysis of covariance (ANCOVA) was used to control for pH with Tukey's HSD post-hoc tests. Analyses were performed using SPSS 13 (SPSS Inc., USA).

Brain pH was significantly correlated with SELENBP1 gene expression (r=−0.375, P<0.01). Lower pH has previously been noted to be associated with mRNA degradation (Harrison et al. 1999; Kingsbury et al. 1995), but in this study lower pH was related to higher SELENBP1 gene expression. Although this result was counter-intuitive, pH was included in the statistical model for both psychosis and clinical disease group.

Figure 1B:
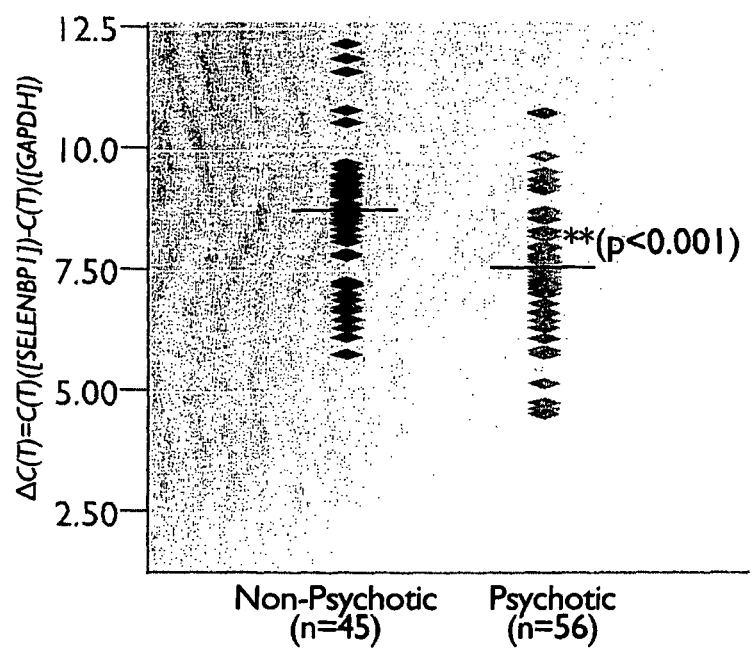
In FIG. 1B the mean values are expressed in psychotic and non-psychotic bipolar individuals as well as schizophrenia and normal controls.

Following comparison of C(T) values across groups, it determined that that SELENBP1 gene expression (controlled for pH) was significantly up-regulated by 12% in the presence of psychosis (ANCOVA, F=11.06, df=2.96, P<0.001, FIG. 1A). For the clinical disease groups, variable levels of SELENBP1 gene expression were also noted (ANOVA, df=4.94, F=5.49, P<0.001). Further analysis revealed that, compared to the control group, there was an 11% increase in SELENBP1 gene expression in the schizophrenia subjects (P=0.045, shown in FIG. 1B) and a 14% increase in the psychotic bipolar disorder group (P=0.027); whereas the non-psychotic bipolar cases were not significantly different from the control group.

Discussion

In this study, the finding that SELENBP1 gene expression was up-regulated in schizophrenic brains compared to tissue from normal control subjects was validated. Furthermore, a stronger significant increase in SELENBP1 gene expression in individuals with an episode of psychosis, as well as in psychotic bipolar cases, was determined, which points to a common mechanism of development of psychosis regardless of clinical group. Elevated SELENBP1 may predispose one to psychosis or may be elevated following development of psychosis. Alternatively, elevated SELENBP1 may play a protective and/or compensatory role within the brain following a psychotic episode, or may be in response to antipsychotic medication administration. In order to test the latter possibility, the correlation between SLENBP1 expression and lifetime levels of exposure to antipsychotic medication (in fluphenazine equivalents (mg)) was investigated; however, no significant evidence of a relationship was found (r=−0.04, P=0.695). This is consistent with other work on brain samples from the National Brain Databank, in which up-regulation of SELENBP1 in schizophrenia was unexplained by exposure to antipsychotic or other psychotropic medications.

Apart from its role in binding selenium, SELENBP1 has been located in the golgi apparatus, is localized to the growing tips of neurons, and has been associated with ovarian cancer (Huang et al. 2006). An epidemiological study has shown that regions of the United States with selenium deficiency in the soil are associated with higher frequencies of schizophrenia (Brown 1994) and other studies have demonstrated that selenium deficiency can directly regulate glutamate-induced oxidative stress in the brain (Ramaekers et al. 1994; Savaskan et al. 2003).

In conclusion, the finding that mRNA of SELENBP1 is increased in the brains of patients with schizophrenia has been validated, and even more statistically reliable evidence for up-regulation was observed in those patients with psychosis whether in the setting of schizophrenia or bipolar disorder. In terms of clinical utility, the expression of SELENBP1 can be used as a biomarker to independently diagnose both psychosis and schizophrenia.

Example 2

Materials and Methods

Selenium binding protein gene (SELENBP1) and GAP-43 (a pre-synaptic gene) were examined as biomarkers of psychosis. mRNA expression was measured in the dorsolateral-prefrontal cortex (dlPFC, BA 46) of 34 schizophrenia, 33 bipolar disorder (20 with psychosis) and 34 normal controls.

RNA samples from fresh-frozen dlPFC were purified by the Stanley Foundation using samples from the Stanley Array Collection. The Array Collection consists of the brains from 35 patients with schizophrenia, 35 with bipolar disorder and 35 matched non-psychiatric controls and are described elsewhere. One bipolar disorder case was excluded from the study due to cerebral autosomal dominant arteriopathy with subcortical infarcts and leukoencephalopathy. In addition RNA from one patient sample from each of the groups failed to yield sufficient QPCR signal and were therefore also excluded from the analyses. The demographic variables of utilized samples are summarized in Table 1 above. Of the remaining bipolar cases 20 were diagnosed as psychotic, which together with the 34 schizophrenia cases provided 54 cases with psychosis and 45 who had not been psychotic. The Stanley Foundation assessed RNA quantity using an Agilent Bioanalyzer (Agilent, USA). We confirmed concentrations of RNA by a UV spectrophotometer at 260 nM/280 nM in order to accurately load 1 μg of RNA for cDNA synthesis. cDNA synthesis was then carried out using the iScript cDNA synthesis kit (Bio-Rad, USA) according to the standard protocol.

QPCR was performed using the iQ5 real time system (Bio-Rad, USA) together with Taqman Gene Expression Assay kits (Applied Biosystems, USA) under standard conditions (Canales et al. 2006). Assays containing FAM dye-labeled probes and random octomers for synthesis of SELENBP1 (Assay ID: Hs00187625_m1) and GAP-43 (Hs00176645_m1) were used, along with two housekeeping genes, β-actin (part #:4352668) and GAPDH (part#: 4352666), which have been previously found to be stable in post-mortem brain RNA samples. A dilution series (0.1 ng, 1 ng, 10 ng, and 100 ng) for fl-actin and GAPDH was carried out in five randomly chosen cases to determine the appropriate amount of cDNA for QPCR runs. Loading 10 ng of cDNA produced consistent results across cases and this concentration was used for assessing gene expression of the genes of interest. Within each plate, RNase free water was loaded as a negative control with each gene, and cases were run as duplicates within individual 96-well plates to control for variability in pipetting and cycling conditions. GAPDH was employed as the housekeeping gene for normalizing individual C(T)'s for the candidate genes prior to statistical analyses as it was less variable than β-actin.

In the first step of analysis, demographic variables that predicted outcome of gene expression at the P<0.10 level using a Pearson's correlation was assessed. These variables, together with other variables with a potential of affecting gene expression, were then controlled for in the final statistical model. For comparisons of SELENBP1 in either the presence of psychosis or clinical disease groups a univariate analysis of covariance (ANCOVA) was used to control for pH with Tukey's HSD post-hoc tests. As the rest of the candidates had known functional influences on one another, group differences were assessed using a multivariate model (MANCOVA) and relevant covariates controlled for where they impacted on expression levels of two or more genes across all cases also at P<0.10. Analyses were performed using SPSS 13 (SPSS Inc., USA).

Results

For the potential effect of confounding variables, only brain pH was significantly correlated with SELENBP1 gene expression (r=−0.375, P<0.01), while the other variables did not show any significance with the candidate genes. Lower pH has previously been noted to be associated with mRNA degradation, but in this study, lower pH was related to higher SELENBP1 gene expression and although counter-intuitive, pH was included in the statistical model for both psychosis and clinical disease group.

Following comparison of C(T) values for the candidate genes across groups, it was determined that pH controlled SELENBP1 gene expression was significantly up-regulated by 12% in the presence of psychosis (ANCOVA, F=11.06, df=2, P<0.001). For the clinical disease groups, the increase in SELENBP1 gene expression was also noted (ANOVA, df=3, F=3.826, P<0.001), even when pH was included as a covariate (P=0.019). Further analysis revealed that compared to the control group there was an 11% increase in SELENBP1 gene expression in the schizophrenia subjects (P=0.015) and a 14% increase in the psychotic bipolar group (P=0.007), whereas the non-psychotic bipolar cases were not significantly different from the control group. GAP-43 (F=3.946, df=3), P=0.011) was increased by 22% in psychotic bipolar (P=0.002) and 18% in non-psychotic bipolar subjects (P=0.038) compared to controls. Additionally, brain weight was positively correlated with expression of GAP-43 (r=0.234, P=0.019).

Discussion

A significant increase in SELENBP1 gene expression in individuals with an episode of psychosis was found, SELENBP1 gene expression was also elevated in schizophrenia, validating previous finding (Glatt 2005), as well as in psychotic bipolar cases, which points to a common mechanism of development of psychosis regardless of clinical group.

In addition, it was determined that gene expression of GAP-43 was increased in the brains of patients with bipolar disorder versus controls. The expression of both SELENBP1 and GAP-43 can be used as biomarkers to independently diagnose both psychosis and bipolar disorder. In conclusion, the finding that mRNA for SELENBP1 is increased in the brains of patients with schizophrenia has been confirmed, and even more robustly in those patients with psychosis whether in the setting of schizophrenia or bipolar disorder.

BIBLIOGRAPHY

Brown J S, Jr. Schizophr Bull 1994; 20:387-98.
Brzustowicz L M, et al. Science 2000; 288:678-682.
Canales R D, et al. Nat Biotechnol 2006; 24:1115-22.
Chen and Chen, Neuropsychopharmacology 2005; 30:268-277.
Dempster, et al. BMC Med Genet 2006; 7:10.
Glatt S J, et al. Proc Natl Acad Sci USA 2005; 102:15533-8.
Halim N D, et al. Mol Psychiatry 2003; 8:797-810.
Harrison P J, Brain 1999; 122:593-624.
Harrison P J, Brain 2002; 125:1428-49.
Harrison P J, Neurosci Lett; 1995; 200; 151-514.
Huang K C, et al. Int J Cancer 2006; 118:2433-40.
Jurewicz I, et al. Eur Neuropsychopharmacol 2001; 11:395-398.
Ketter T A, et al. J Psychiatr Res 2004; 38:47-61.
Kingsbury A E, et al. Brain Res Mol Brain Res 1995; 28(2): 311-8.
Lipska et al. Biol. Psychiatry 2006; 60:650-658.
Livak and Schmittgen Methods 2001; 25:650-658.
Mimmack ML, et al. roc Natl Acad Sci USA 2002; 99:4680-4685.
Mimics K et al. Trends Neurosci 2001; 24:479-486.
Miyaguchi K Histochem Cell Biol 2004; 121:371-6.
Mufson E J, et al. Prog Brain Res 2006; 158:197-222.
Potash J B, et al. Am J Psychiatry 2003; 160:680-686.
Preece and Cairns Brain Res Mol Brain Res 2003; 118:60-71.
Ramaekers, V T et al. Neuropediatrics 1994; 25:217-223
Scarr E, et al. Bipolar Disord 2006; 8:133-43.
Savaskan N E, et al. Faseb J 2003; 17:112-4.
Soverchia L, et al. Addict Biol 2005; 10:5-13.
Vawter M P, et al. Schizophr Res 2002; 58:11-20.
Webster M J, et al. Schizophr Res 2001; 49:89-98.
Xu B, et al. PLoS Med 2005; 2:e263.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to diagnose bipolar disorder comprising measuring an amount of growth associated protein 43 (GAP-43) in a first biological sample from a subject; and diagnosing bipolar disorder in said subject based on if a higher amount of GAP-43 is in the first biological sample relative to an amount of GAP-43 in a second biological sample from an individual without bipolar disorder.

2. The method of claim 1, wherein the bipolar disorder is non-psychotic bipolar disorder.

3. The method of claim 1, wherein the bipolar disorder is psychotic bipolar disorder.

4. The method of claim 1, wherein the amount of GAP-43 RNA is measured.

5. The method of claim 1, wherein the amount of GAP-43 protein is measured.

6. The method of claim 1, wherein the method confirms a previous diagnosis of bipolar disorder.

7. A method to diagnose psychotic bipolar disorder comprising measuring an amount of SELENBP1 and growth associated protein 43 (GAP-43) in a first biological sample from a subject; and diagnosing psychotic bipolar disorder in said subject based on if a higher amount of SELENBP1 and GAP-43 is in the first biological sample relative to an amount of SELENBP1 and GAP-43 in a second biological sample from an individual without psychotic bipolar disorder.

8. The method of claim 7, wherein the method confirms a previous diagnosis of psychotic bipolar disorder.

9. A method to diagnose psychosis comprising: measuring if an amount of SELENBP1 in a first biological sample from a subject having bipolar disorder is at least 12% higher than an amount of SELENBP1 in a second biological sample from a non-psychotic individual; and diagnosing an episode of psychosis in the subject based on if the amount of SELENBP1 in the first sample is at least 12% higher.

10. The method of claim 9, wherein the subject and individual are mammalian.

11. The method of claim 10, wherein the mammal is human.

12. The method of claim 9, wherein the first and second samples comprise brain.

13. The method of claim 9, wherein the amount of SELENBP1 RNA is measured.

14. The method of claim 9, wherein the amount of SELENBP1 protein is measured.

15. The method of claim 9 wherein the method confirms a previous diagnosis of psychosis.

* * * * *

UNITED STATES PATENT AND TRADEMARK OFFICE
CERTIFICATE OF CORRECTION

| | | |
|---|---|---|
| PATENT NO. | : 8,470,299 B2 | Page 1 of 1 |
| APPLICATION NO. | : 12/600119 | |
| DATED | : June 25, 2013 | |
| INVENTOR(S) | : Ming T. Tsuang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this
Thirteenth Day of May, 2014

Michelle K. Lee
*Deputy Director of the United States Patent and Trademark Office*